United States Patent [19]

Suzuki

[11] Patent Number: 5,172,678
[45] Date of Patent: Dec. 22, 1992

[54] DEVICE FOR DETERMINING ACTIVATION OF AN AIR-FUEL RATIO SENSOR

[75] Inventor: Hiroyoshi Suzuki, Himeji, Japan

[73] Assignee: Mitsubishi Denki Kabushiki Kaisha, Tokyo, Japan

[21] Appl. No.: 842,624

[22] Filed: Feb. 27, 1992

[30] Foreign Application Priority Data

Apr. 2, 1991 [JP] Japan ................................. 3-069845

[51] Int. Cl.$^5$ ........................................... F02D 41/14
[52] U.S. Cl. ..................................... 123/688; 123/697
[58] Field of Search ................ 123/688, 697; 204/425, 204/466

[56] References Cited

U.S. PATENT DOCUMENTS

| | | | |
|---|---|---|---|
| 4,505,246 | 3/1985 | Nakajima et al. | 123/688 |
| 4,860,712 | 8/1989 | Nakajima et al. | 123/697 |
| 4,889,098 | 12/1989 | Suzuki et al. | 123/697 X |
| 4,895,123 | 1/1990 | Uchinami et al. | 123/688 |
| 5,036,820 | 8/1991 | Fujimoto et al. | 123/688 X |
| 5,054,452 | 10/1991 | Denz | 123/688 X |

FOREIGN PATENT DOCUMENTS 0294355 12/1986 Japan.
0009357 1/1989 Japan.

*Primary Examiner*—Willis R. Wolfe
*Attorney, Agent, or Firm*—Sughrue, Mion, Zinn, Macpeak and Seas

[57] ABSTRACT

A device for determining activation of an air-fuel ratio sensor which comprises an air-fuel ratio sensor comprising an air-fuel ratio sensor comprising an oxygen concentration cell element and an oxygen pump element arranged in an exhaust system of an engine provided with electrodes and an interposing diffusion chamber wherein exhaust gas is diffused and introduced, and a heater for heating the oxygen concentration cell element and the oxygen pump element; a pump current controlling means for controlling pump current which flows in the pump element so that the electromotive force of the concentration cell element becomes a predetermined reference voltage; a pump current detecting means; a pump current cutting means; a pump voltage detecting means; a heater power supplying means; a memorizing means for memorizing a previous pump voltage allowable range for the pump current or a target air-fuel ratio of the engine; and a timer means operated at every predetermined time interval for starting the heater supplying power means to the heater during a pump-current-cut state and for releasing the cutting supply of the pump current during the predetermined time interval. The air-fuel ratio controlling device detects a pump voltage which determines that the air-fuel ratio sensor is activated when the pump voltage falls from the previously memorized pump voltage allowable range, and then releases the pump-current-cut state.

1 Claim, 7 Drawing Sheets

DEVICE FOR DETERMINING ACTIVATION OF AN AIR-FUEL RATIO SENSOR

The present invention relates to a device for determining activation of an air-fuel ratio sensor which can detect accurately an activation point of an air-fuel ratio sensor without deteriorating the air-fuel ratio sensor which detects an air-fuel ratio of an engine.

In recent times, a system is proposed wherein a whole area air-fuel ratio sensor is provided at an exhaust system to accurately control an air-fuel ratio of an intake mixture of an internal combustion engine to a target value over the whole area of the air-fuel ratio in use, detects exhaust gas components correlating with the air-fuel ratio, and fuel supply quantity is controlled by a feed back control.

Since such an air-fuel sensor does not function unless temperature of a sensor element unit thereof is elevated to about 400° to 500° C. or more, a heater is provided which heats up the sensor element unit, and maintains the temperature of the sensor element unit above an activation temperature. However, when the engine is started up from a state wherein the sensor temperature is low, the sensor may be destructed unless it is utilized after confirming that the sensor unit temperature is above the activation temperature after the heater is initiated.

Various determining methods are proposed for determining the activation of the air-fuel sensor. Among these, for instance, a method is known which determines that the activation of the sensor is completed when a predetermined time elapses after heating of the sensor is performed, as disclosed in Japanese Unexamined Patent Publication No. 241652/1986, or a method is known which determines that the sensor is activated when an interelectrode voltage between a cell element and a pump element falls in a predetermined range when current is flown in the pump element of the sensor. Explanation will be given to this conventional example based on drawings as follows.

FIG. 8 is a construction diagram of a conventional engine control system which performs an air-fuel control utilizing the air-fuel sensor. FIG. 1 is a construction diagram of an example of air-fuel control device of a conventional case and also an invented case, mentioned later, and FIG. 9 designates time charts for explaining a method of initiating the conventional sensor when the sensor is to be initiated. In the followings, explanation will be given to the conventional device, based on FIG. 8 and FIG. 9 (timing charts when the conventional sensor is initiated), utilizing FIG. 1 according to necessity.

In FIG. 8, a reference numeral 1 designates an air-fuel sensor, which is installed at an exhaust pipe 31 of an engine 30, 2, a sensor control amplifier of the air-fuel sensor 1, 3, an engine revolution sensor, 4, an intake quantity sensor, 5, a cooling water temperature sensor of the engine 30, 6, a fuel injection valve, 7, an air-fuel ratio control device, 8, a throttle valve, 9, a throttle opening degree sensor of the throttle valve 8, and 32, an intake pipe.

In FIG. 8, the engine revolution sensor 3 detects an engine revolution number Ne, the intake quantity sensor 4, an intake quantity Qe, the throttle opening degree sensor 8, a throttle opening degree $\theta$, and the cooling water temperature sensor 5, a cooling water temperature WT. These detected values are respectively outputted to the air-fuel ratio control device 7, and are state quantities showing running condition of the engine 30.

The air-fuel ratio of the mixture of intake air introduced to the throttle valve 8, and fuel injected from the fuel injection valve 6 at intake pipe 32, is detected by the air-fuel ratio sensor 1 installed at an exhaust pipe 31, utilizing a sensor control amplifier 2. An output of the air-fuel ratio is transmitted similarly to the air fuel ratio control device 7 from the sensor control amplifier 2.

Next, a detailed construction of the air-fuel ratio sensor 1 is explained by FIG. 1. In FIG. 1, the air-fuel ratio sensor 1 is composed of a sensor element unit 11 and a heater 12. The sensor element unit 11 is composed of an oxygen pump element 11a, an oxygen concentration cell element 11b, a diffusion chamber 11c, and an atmospheric chamber 11d. The sensor control amplifier 2 is composed of a differential integral amplifier as a pump current controlling means 21, a differential amplifier 22 as a pump current detecting means, a non-inverting amplifier 23, a non-inverting amplifier 24 as a pump voltage detecting means, a cut transistor 25 as a pump current cutting means, and a heater control circuit 26.

A voltage of an oxygen concentration cell element 11b is connected to an inverting input terminal of the differential integral amplifier 21, and a reference voltage Vref, to a non-inverting terminal thereof. An output of the differential integral amplifier 21 is inputted to the oxygen pump element 11a through a current detecting resistance Rs. A both terminal voltage of the current detecting resistance Rs is inputted to non-inverting input terminal and an inverting input terminal of the differential amplifier 22. An output terminal of the non-inverting amplifier 23 is connected to an inverting input terminal thereof and an output of the differential amplifier 22 is connected to a non-inverting input terminal of the non-inverting amplifier 23. An offset voltage $V_{OB}$ is connected to the inverting input terminal thereof. A voltage which is applied to the oxygen pump element 11a is connected to a non-inverting input terminal of the non-inverting amplifier 24, and an offset voltage $V_{PB}$ is connected to an inverting input terminal thereof.

Next, explanation will be given to the construction of the air-fuel ratio control device 7. This air-fuel ratio control device 7 is composed of multiplexors 71a and 71b, analogue/digital (hereinafter A/D) converters 72a and 72b, an input interface (hereinafter I/F) 73, a microprocessor (hereinafter $\mu$-P) 74, a read only memory (hereinafter ROM) 75, a random access memory (hereinafter RAM) 76, output I/Fs 77a and 77b, and a fuel injection valve drive circuit 78. The output Ne of the engine revolution sensor 3 is inputted to the $\mu$-P 74 through the input I/F 73, and the output Qa of the intake quantity sensor 4 and the output WT of the cooling water temperature sensor 5, from the multiplexor 71b through A/D converter 72b. Outputs $V_O$ and $V_{PO}$ of the non-inverting amplifier 23 and the non-inverting amplifier 24 of the sensor control amplifier 2 are transmitted to the $\mu$-P 74 from the multiplexor 71a through the A/D converter 72a. Furthermore, the fuel injection valve 6 is connected to the fuel injection valve drive circuit 78 which is controlled through the output I/F 77a as well as the cut transistor 25 and the heater control circuit 26.

Next, explanation will be given to the operation of this conventional example. In a state wherein the engine 30 is driven, the heater 12 of the air-fuel sensor 1 is controlled to operate by the heater control circuit 26, and the sensor element unit 11 is activated, the oxygen concentration cell element 11b generates an electromotive force Vs which corresponds with a difference of oxygen concentration between in the diffusion chamber 11c and the atmospheric chamber 11d.

When this sensor electromotive force Vs is controlled by flowing a pump current $I_P$ to the oxygen pump element 11a so that it becomes the reference voltage Vref through the dimensional integral amplifier 21 and a current detecting resistance Rs, the pump current $I_P$ is proportional to the air-fuel ratio.

At this occasion, this pump current $I_P$ is detected by the detecting resistance Rs, which is amplified by the differential amplifier 22, and provided with an offset voltage $V_{OB}$ by the non-inverting amplifier 23, by which the air-fuel ratio output $V_O$ is obtained. The direction of the offset voltage $V_{OB}$ differs between in case of an excessively rich zone of the air-fuel ratio and that of an excessively lean zone thereof. Therefore, the offset voltage $V_{OB}$ is provided to make the air-fuel ratio output $V_O$ a positive output irrespective of the direction of the pump current $I_P$.

The air-fuel ratio control device 7 calculates a target air-fuel ratio by the μ-P 74 from informations of the revolution number Ne, intake quantity Qa, the throttle opening degree $\theta$ and the cooling water temperature WT based on programs and data previously memorized in the ROM 75. The air-fuel ratio control device 7 performs a feed back control so that the air-fuel ratio of the engine 30 becomes the target air-fuel ratio by correcting a valve opening time of the fuel injection valve 6, based on a deviation between the target air-fuel ratio and an actual air-fuel ratio which is converted from the measured air-fuel ratio output $V_O$ and injecting fuel from the fuel injection valve 6 corresponding to the valve opening time. The RAM 76 is utilized for memorizing the data temporarily at this occasion.

FIG. 9 illustrates timing charts when the air-fuel ratio sensor is initiated. Explanation will be given to an example wherein the air-fuel ratio is rich after the engine is started. The heater 12 of the air-fuel ratio sensor 1 starts heating by a drive order which is given to the heater control circuit 26 from the μ-P 74 through the output I/F 77a simultaneously with the starting of the engine 30.

At this occasion, in a range of the temperature Ts of the sensor element unit 11 of below about 400° C., since the electromotive force Vs of the oxygen concentration cell element 11b stays low, input deviation of the differential integral amplifier 21 is large. Accordingly, a large pump voltage $V_p$ is applied to the pump element 11a.

The pump voltage output $V_{PO}$ becomes a positive output wherein the pump voltage $V_p$ is added with the offset voltage $V_{PB}$ at the non-inverting amplifier 24. Since impedance of the pump element 11a is high, almost no pump current $I_p$ is flown, and the air-fuel ratio output $V_O$ is almost equal to the offset voltage $V_{OB}$.

Furthermore, when the temperature Ts approaches to about 400° to 500° C., since the electromotive force Vs of the oxygen concentration cell element 11b is increased to the reference voltage Vref, the sensor electromotive force Vs is controlled constant to the reference Vref. Therefore, the pump voltage $V_p$ converges in the direction wherein oxygen is supplied to the diffusing chamber 11c, that is, in the direction wherein $V_{PO} \leq V_{PB}$, the pump current $I_p$, gradually to a current value showing current air-fuel ratio, and the conversion is completed at the temperature Ts of about 700° C.

Accordingly, conventionally, as is illustrated, to detect the activation point, an activation determining method is proposed wherein the activation is determined when the pump voltage output $V_{PB}$ falls in a predetermined allowable voltage range of $V_{PB} \pm \Delta V_{PB}$, or an activation determining method is proposed wherein the sensor is determined to be activated, when the difference $\Delta V_s$ between the sensor electromotive force Vs and the reference voltage Vref falls in a predetermined range and a pump voltage output $V_{PB}$ falls in a predetermined allowable voltage range of $V_{PB} \pm \Delta V_{PB}$.

However, in the conventional activation determining method, since a large voltage is continuously applied to the pump element 11a, in a state wherein the temperature of the sensor element unit 11 is low, the deterioration of the sensor is accelerated and the durability of the sensor is low. To solve the above problem, a method is proposed wherein a timer is provided after the initiation of the air-fuel sensor, the pump current is stopped flowing to the oxygen pump element 11a by making the cut transistor 25 ON in this timer period, and the pump current restarts flowing to the oxygen pump element 11a by making the cut transistor 25 OFF after the timer period is terminated.

However, an index of the sensor characteristics can not be obtained during the timer period. Accordingly, in case that the running condition of the engine changes after the starting up of the engine, and the temperature elevation of the sensor element unit 11 is reduced, the sensor may not be activated even after the timer period is terminated. On the contrary, when the temperature elevation of the element unit 11 is fast as in the case in which the engine is restarted after running, the timer period may not be terminated regardless of a case wherein the air-fuel sensor 1 is already activated. Therefore, the accurate determination of the activation point is difficult.

It is an object of the present invention to solve above problems. It is an object of the present invention to provide a device for determining activation of an air-fuel ratio sensor capable of detecting accurately the activation point of the air-fuel sensor without deteriorating the air-fuel sensor, and capable of determining the activation similarly even when the air-fuel ratio sensor enters into an inactive zone again after the air-fuel ratio sensor is once activated.

According to an aspect of the present invention, there is provided a device for determining activation of an air-fuel ratio sensor which comprises:

an air-fuel ratio sensor comprising an oxygen concentration cell element and an oxygen pump element arranged at an exhaust system of an engine made of an oxygen-ion-conductive-solid-electrolyte material respectively provided with electrodes and interposing a diffusion chamber wherein exhaust gas of the engine is diffused and introduced, and a heater which heats the oxygen concentration cell element and the oxygen pump element;

a pump current controlling means for controlling pump current which flows in the oxygen pump element so that electromotive force of the oxygen concentration cell element becomes a predetermined reference voltage;

a pump current detecting means for detecting the pump current controlled by the pump current controlling means;

a pump current cutting means for cutting supply of the pump current;

a pump voltage detecting means for detecting pump voltage applied to the oxygen pump element;

a heater power supplying means for supplying power to the heater;

a memorizing means for previously memorizing a pump voltage allowable range for the pump current or a target air-fuel ratio of the engine;

a timer means for starting supplying power to the heater from the heater supplying power means in a pump-current-cut state and for releasing the cutting supply of the pump current during a predetermined time interval from starting time of supplying power at every predetermined time period; and an air-fuel ratio controlling device which has the pump current controlling means control the pump current, detects a pump voltage, determines that the air-fuel sensor is activated when the pump voltage falls in the previously memorized pump voltage allowable range, and releases the pump-current-cut state.

In this invention, the power supply to the heater is initiated by the heater power supplying means in a pump-current-cut state, and the pump current control is performed by the pump current controlling means by releasing the pump current cutting for a predetermined time interval from time of the initiation at every predetermined period by the timer means. By measuring the pump voltage by detecting the pump current flowing in the oxygen pump element by the pump current detecting means, the air-fuel ratio sensor is determined to be activated when the pump voltage falls in a previously memorized pump voltage allowable range, and the pump-current-cut state is released.

Figure 1:
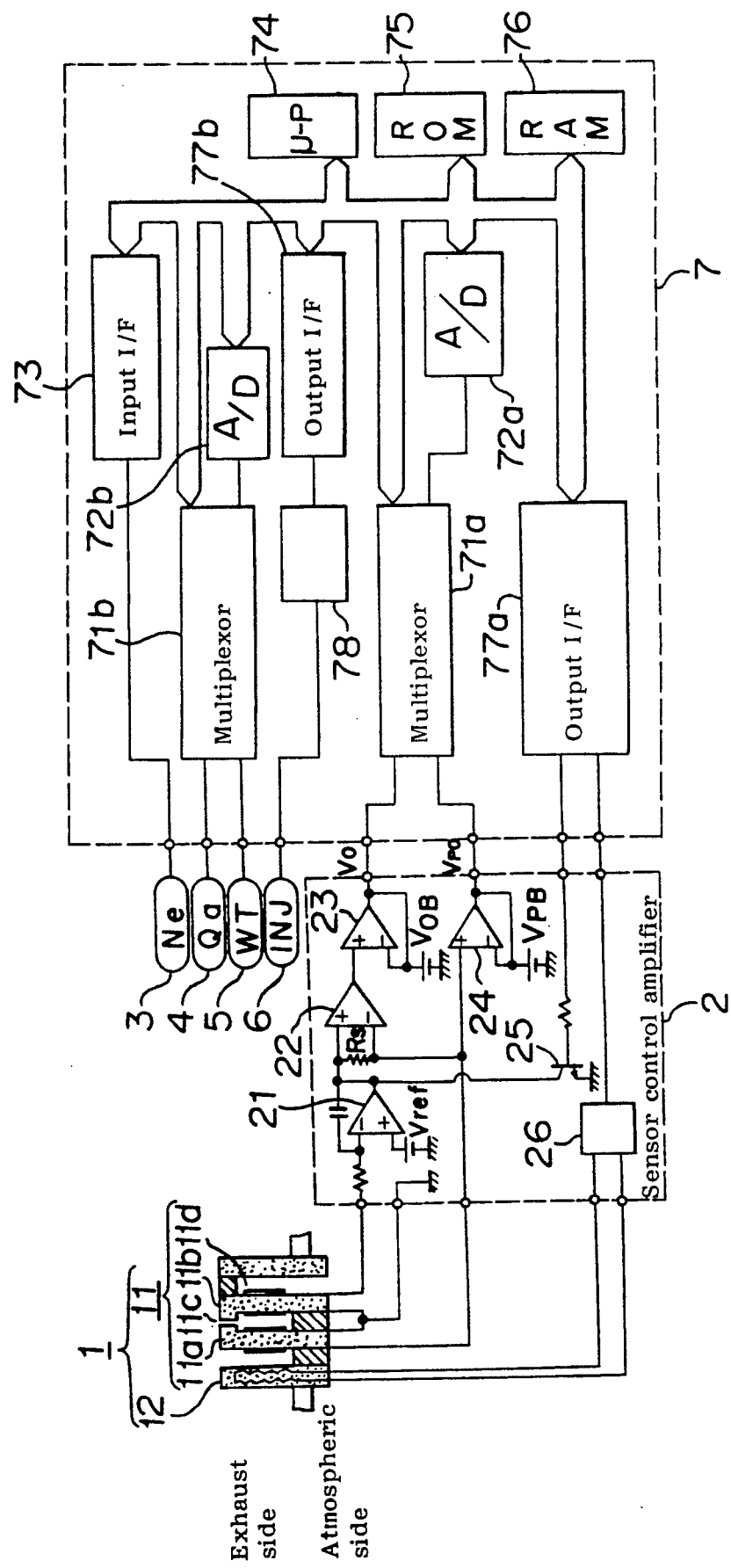
FIG. 1 is a construction diagram of an example of a device for measuring activation of an air-fuel ratio sensor according to the present invention.

In the followings, explanation will be given to embodiments of a device for determining activation of an air-fuel ratio sensor according to the present invention. FIG. 1 is a construction diagram of an embodiment thereof, which is the same with the above-mentioned conventional example in its construction. Therefore, further explanation is omitted as for the construction. The procedure for determining activation of the air-fuel ratio sensor in this invented device is different from that in the conventional case.

Figure 2:
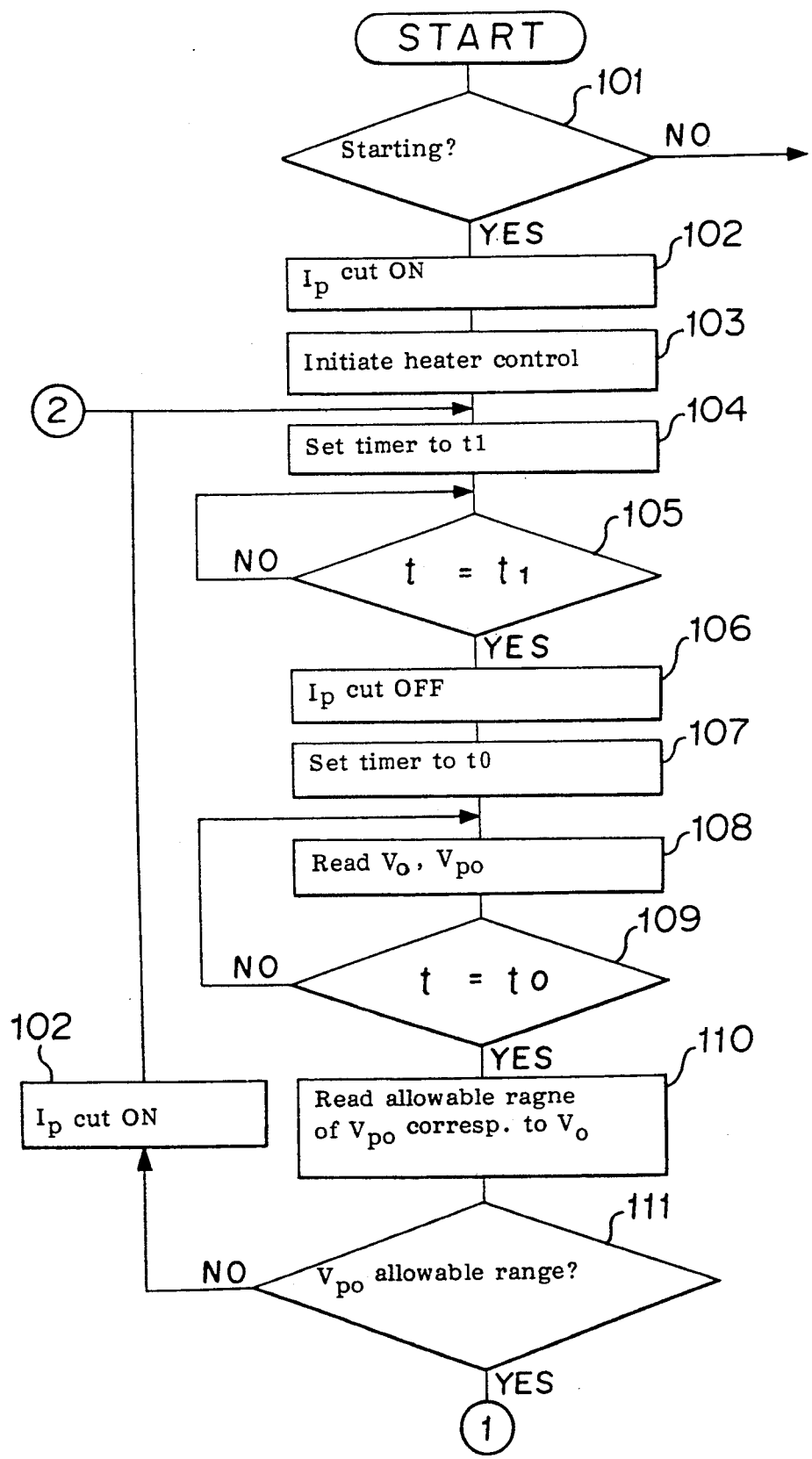
FIG. 2 is a flow chart showing a first example of a procedure for measuring the activation of a device for determining the activation of the air-fuel sensor.
Figure 5:
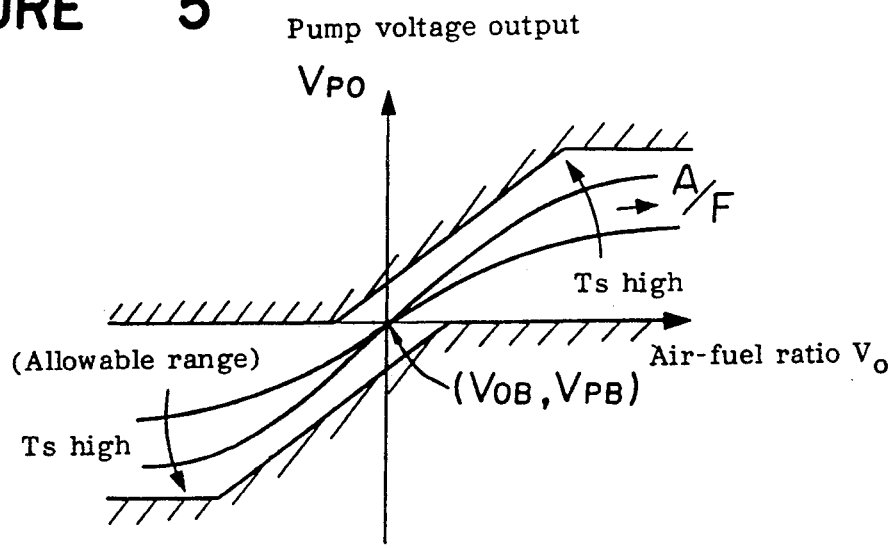
FIG. 5 is an explanatory diagram showing an allowable pump voltage range for the air-fuel ratio output in the device for measuring the activation of the air-fuel ratio sensor according to the present invention.
Figure 7:
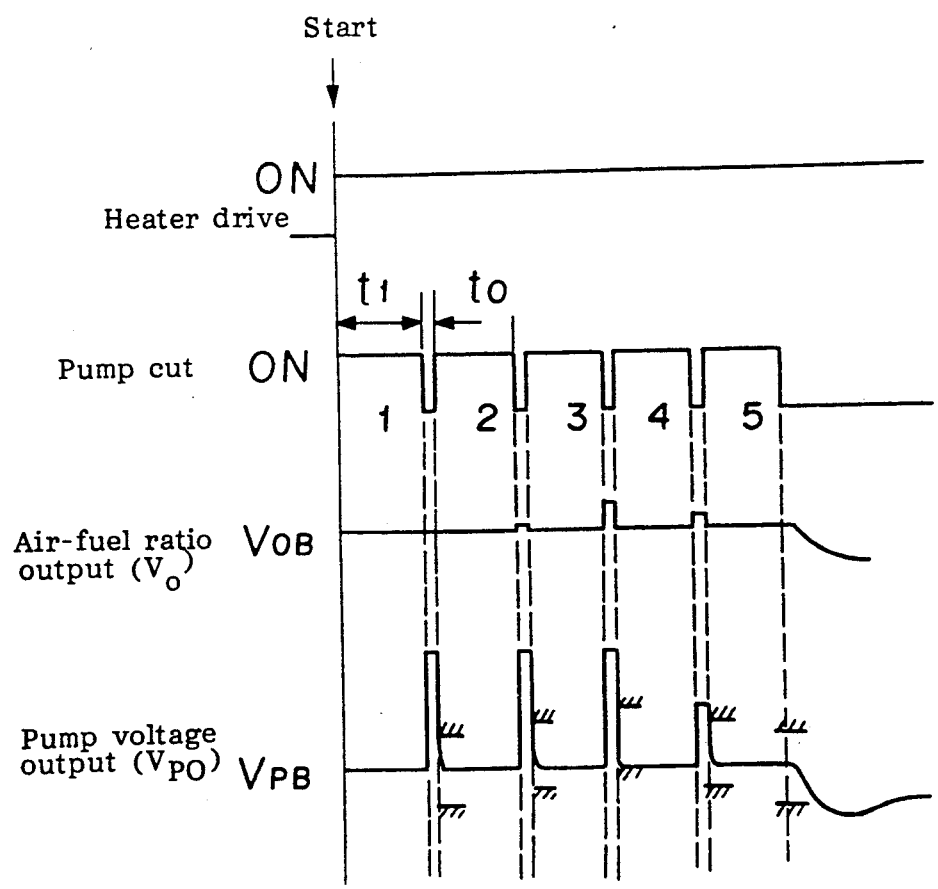
FIG. 7 illustrates timing charts in the initiation of the sensor by an activation procedure in the device for the activation of the air-fuel ratio sensor according to the present invention.

FIG. 2 is a flow chart for explaining the determination procedure of the activation of the air-fuel ratio sensor by this invented device, FIG. 5, a diagram showing a previously memorized allowable pump current range for the air-fuel ratio output, and FIG. 7, timing charts in the initiation of the air-fuel ratio sensor when the activation determination is performed by this invention.

Figure 8:
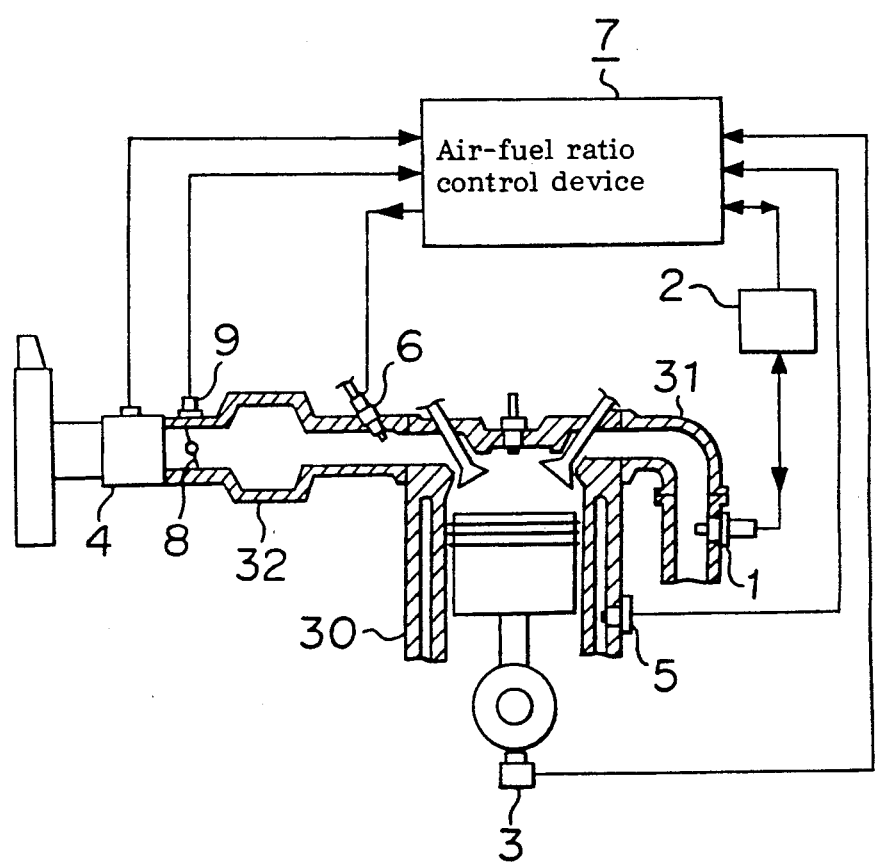
FIG. 8 is a construction diagram of an engine control system applied to a conventional method of measuring the activation of the air-fuel ratio sensor.

First, when the engine 30 shown in FIG. 8 is started up, the operation determines whether the engine is in starting mode by the $\mu$-P 74 of the air-fuel ratio control device 7, at step 101 of FIG. 2. When the engine is in starting mode, the operation in step 102 makes the cut transistor 25 of the sensor control amplifier 2 through the output I/F 77a ON, and performs pump current cut ($I_p$ cut) so that the pump current is not flown by earthing electric potential of the oxygen pump element 11a. In step 103, the operation initiates the heater control circuit 26 similarly through the output I/F 77a, by which power is supplied to the heater 12, and heating of the sensor element unit 11 is initiated.

Next, in step 104, as shown in FIG. 7, the operation initiates the timer by which a predetermined time t1 is set. When the time t1 elapses in step 105, the operation makes the cut transistor 25 OFF in step 106, by which an output voltage of the differential integral amplifier 21 is applied to the oxygen pump element 11a, so that the electromotive force of the oxygen concentration cell element 11b agrees with the reference voltage Vref, and the pump current $I_p$ is flown by this voltage.

Next, in step 107, with release of the pump current cutting in step 106, the operation sets time t0 as shown in FIG. 7, and continues the release of the pump current cutting during the period of the time t0. During that time, in step 108, the air-fuel ratio output $V_O$ which corresponds with the pump current $I_p$, and the pump voltage output $V_{PO}$ which corresponds with the pump voltage $V_p$ are read in the $\mu$-P 74 after being converted by A/D conversion by the A/D converter 72a through the multiplexor 71a.

The duration of time of the time t0 depends on responsiveness of the sensor and PI constant of the differential integral amplifier 21, and it may be around 10 msec, and may be a short period of about 1 to 5% of the time t1.

Figure 6:
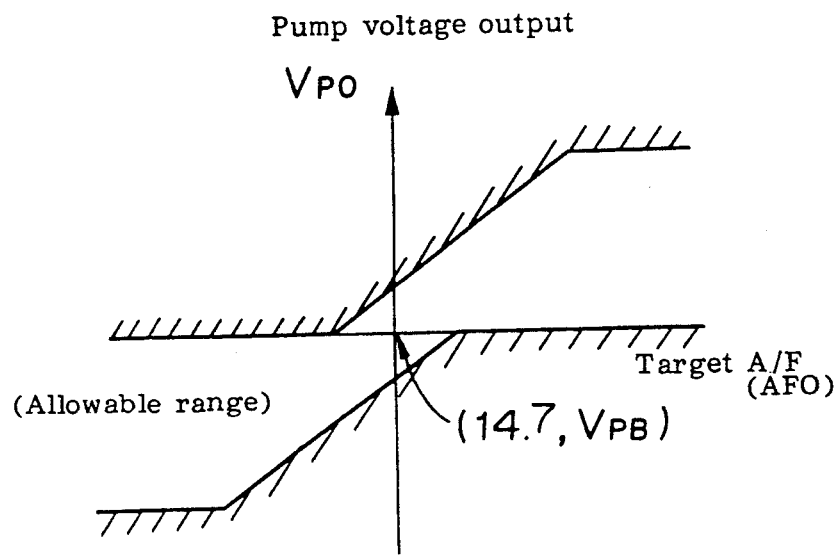
FIG. 6 is an explanatory diagram showing an allowable pump voltage range for a target air-fuel ratio in the device for measuring the activation of the air-fuel ratio sensor according to the present invention.

In step 109, when the time t0 elapses, the operation reads out a pump voltage output allowable range map shown in FIG. 6 which is previously memorized in the ROM 75 in step 110 using the air-fuel ratio output $V_O$ and the pump voltage output $V_{PO}$ just before the elapse. In step 111, the operation determines whether the pump voltage output $V_{PO}$ falls in the allowable range of $V_{PO}$ which corresponds with the air-fuel ratio output $V_O$.

As a result of the determination, when the pump voltage output $V_{PO}$ is out of the allowable range, in step 102, the operation performs the pump current cutting again, and iterates the treatment procedure from step 104 to step 111. When it falls in the allowable range, the operation determines the air-fuel ratio sensor is activated and transfers to a succeeding treatment.

As shown in FIG. 5, in the pump current in which the sensor electromotive force Vs is controlled constant to the reference voltage Vref or the pump voltage corresponding to the air-fuel ratio output $V_O$, that is, the pump voltage output $V_{PO}$, the lower the sensor element temperature Ts, the larger the deviation from the offset voltage $V_{PB}$, and it becomes a maximum output irrespective of the air-fuel ratio in case wherein the electromotive force Vs is not controlled constant to the reference voltage Vref.

Accordingly, by setting the pump voltage output allowable range in an area surrounded by the hatching of the diagram, the determination of the activation temperature of the sensor element can accurately be performed.

FIG. 7 illustrates timing charts for showing a determination of activation when the engine is started. With the starting up of the engine 30, the heater 12 is driven, the behaviors of the air-fuel ratio output $V_O$ and the pump voltage output $V_{PO}$ are shown when the pump current cutting is released in the period of the time t0 at an interval of the time t1 by the timer. At the same time, the pump voltage output allowable range for the air fuel ratio output $V_O$ is shown by the hatched area. In this diagram, the pump voltage output $V_{PO}$ falls in the allowable range in the fifth timer period, the activation determination is performed, and the pump current cutting is released.

Figure 9:
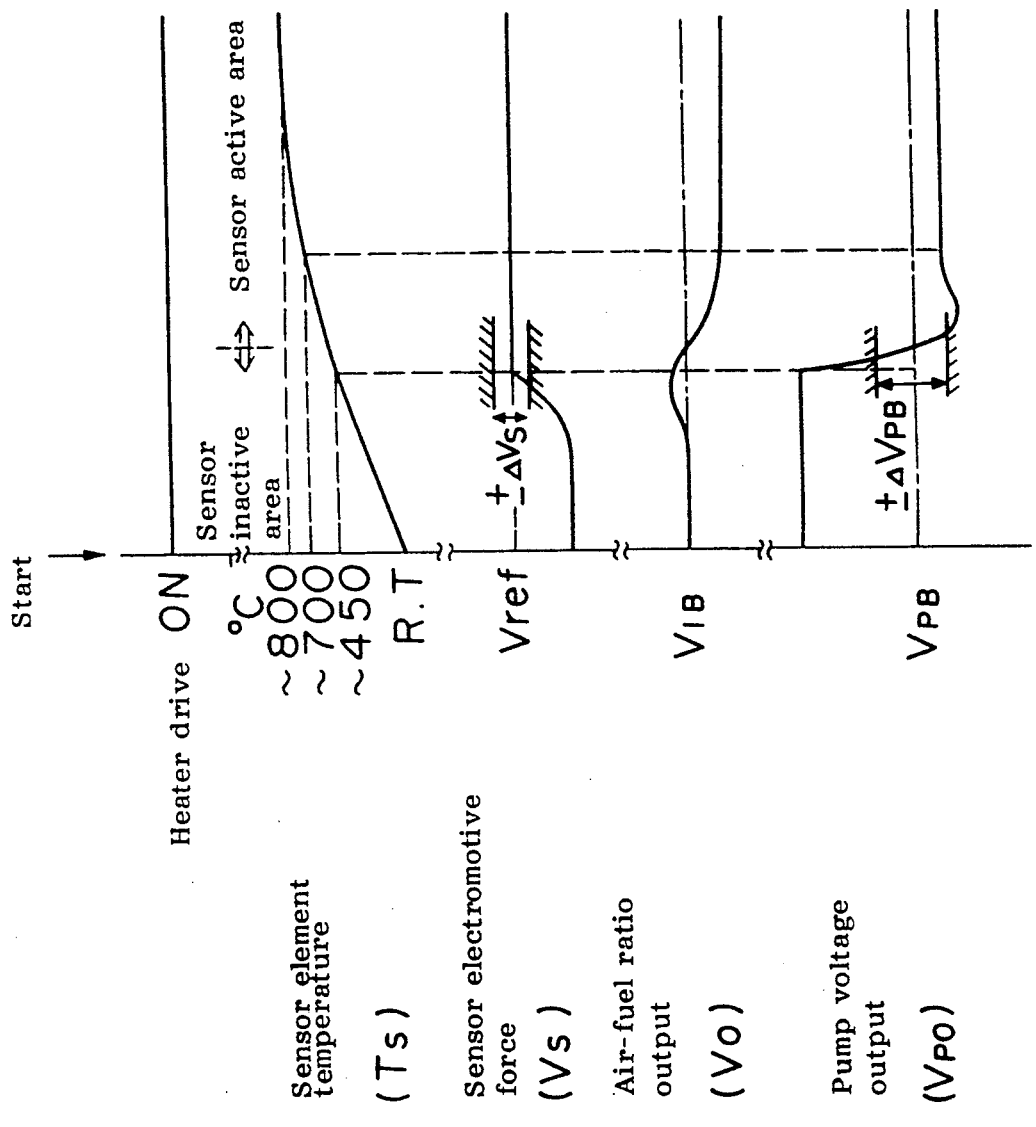
FIG. 9 illustrates timing charts in the initiation of the sensor applied to a method of measuring the activation of the conventional air-fuel ratio sensor.

Although not particularly illustrated, as apparent by comparing this diagram with FIG. 9 showing the initiation behavior by the conventional method, the element temperature Ts at the activation determination is about 500° C.

Accordingly, the above example has an advantage wherein the air-fuel sensor 11 is not deteriorated and destructed by the activation determination treatment, since the voltage is applied to the oxygen pump element 11 only during an extremely short period of the time t0 when the sensor element temperature is too low to establish the constant control of the electromotive force of the sensor. Also it has an advantage wherein the activation determination can accurately be performed irrespective of the starting up air-fuel ratio, since the pump voltage output allowable range which determines the activation by the sensor output $V_O$, is alterated.

Figure 3:
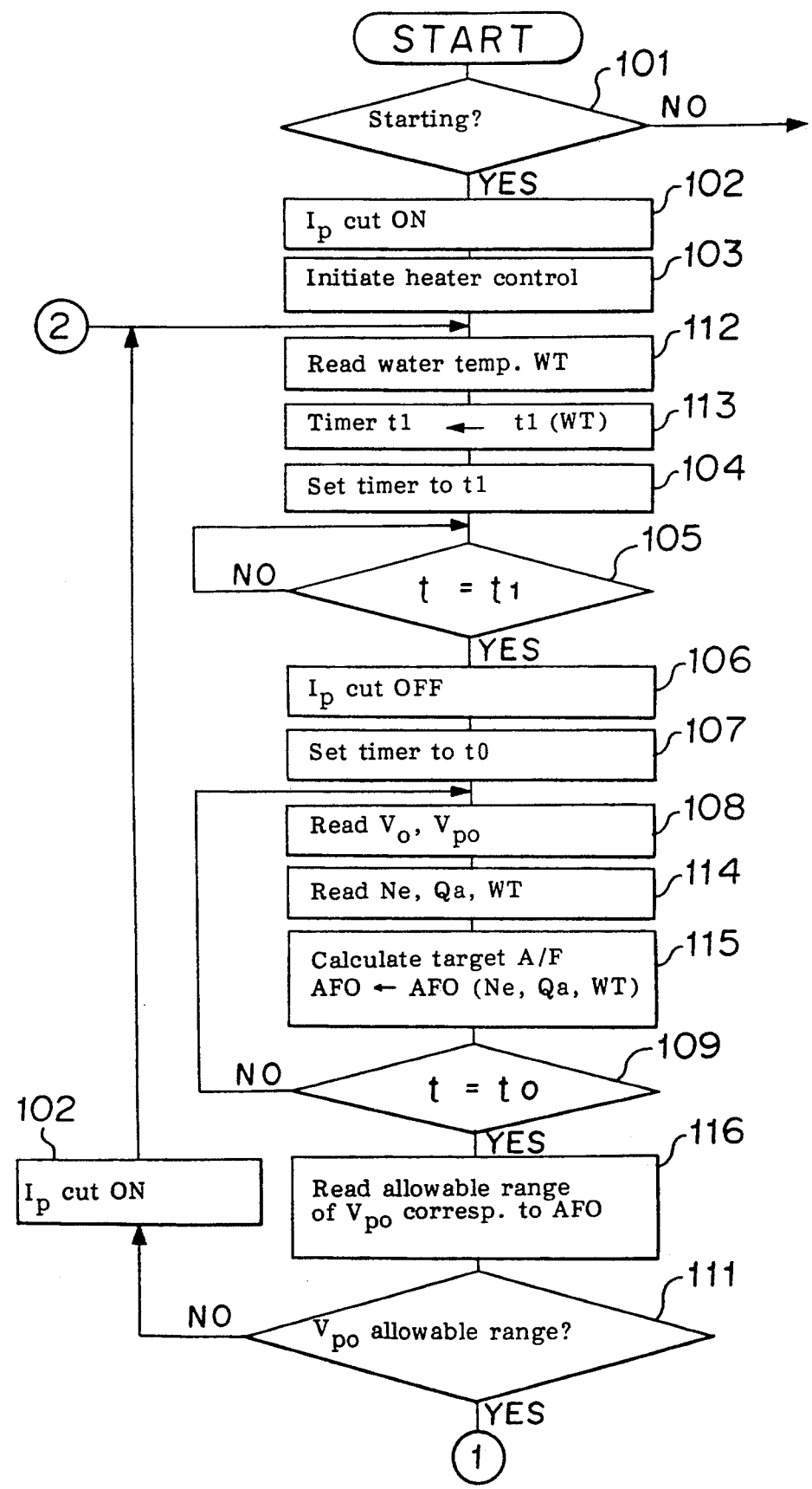
FIG. 3 is a flow chart showing a second example of a procedure for measuring the activation by the device for determining activation of the air-fuel ratio sensor according to the present invention.

Next, explanation will be given to a second example of this invention. FIG. 3 is a flow chart showing a procedure of determining activation of the air-fuel ratio sensor according to the second example, and FIG. 6, a diagram showing an allowable pump voltage range for a previously memorized target air-fuel ratio according to the second example.

In FIG. 3, the treatment of steps 101 and 102 are the same with the steps 101 and 102 in FIG. 2. When the heater control is initiated in step 103, in step 112, the cooling water temperature WT is detected by the cooling water temperature sensor 5, which is A/D-converted by the A/D convertor 72b through the multiplexor 71b, and read in by the μ-P 74.

Next, in step 113, a value of the time t1 is determined as a decreasing function t1 (WT) with respect to the cooling water temperature WT, and similarly in step 104, the time t1 (WT) is set.

At this occasion, when the temperature of the exhaust pipe 31 (FIG. 8) installed with the air-fuel sensor 1 is comparatively elevated and temperature elevation of the exhaust gas is fast as in restarting of the engine in a short period after running, the activation of the sensor element is also fast. In this case, when the cooling water temperature WT is high, the period of the time t1 is reduced and therefore, it has an advantage wherein the determination of the activation is not retarded by the timer.

Next, when the time t1 elapses in step 105, with the release of the pump current cutting in 106, in step 107, the operation sets the time t0. In step 108, the operation reads the sensor output $V_O$ and the pump voltage output $V_{PO}$. In step 114, the operation reads the engine revolution number Ne, the intake quantity Qa, and the cooling water temperature WT which show the running condition of the engine. In step 115, the operation calculates a target air-fuel ratio AFO compatible with the engine revolution number Ne, the intake quantity Qa and the cooling water temperature WT.

Next, when the time t0 elapses in step 109, the operation reads a previously memorized allowable pump current voltage range for the target air-fuel ratio shown in FIG. 6 from the ROM 75 in step 116, using the target air-fuel ratio AFO just before the elapse of the time t0. In step 111, the operation determines whether it is in the allowable range, and if it is in the allowable range, the operation determines that the sensor is activated. Therefore, an effect similar to the first example is obtained by this second example.

Furthermore, in the above examples, as for the air-fuel ratio output $V_O$ and the pump voltage output $V_{PO}$ which are utilized in the determination, values just before the elapse of the time t0 are utilized among the values of the air-fuel ratio output $V_O$ and the pump voltage output $V_{PO}$ which are iteratively measured in time periods of t0. However, since the duration time of the time t0 is determined considering responses of the air-fuel ratio output $V_O$ and the pump voltage output $V_{PO}$ as stated above, values of the air-fuel ratio output $V_O$ and the pump voltage output $V_{PO}$ which are measured just before the elapse of the time t0 only at one time, may be utilized.

Figure 4:
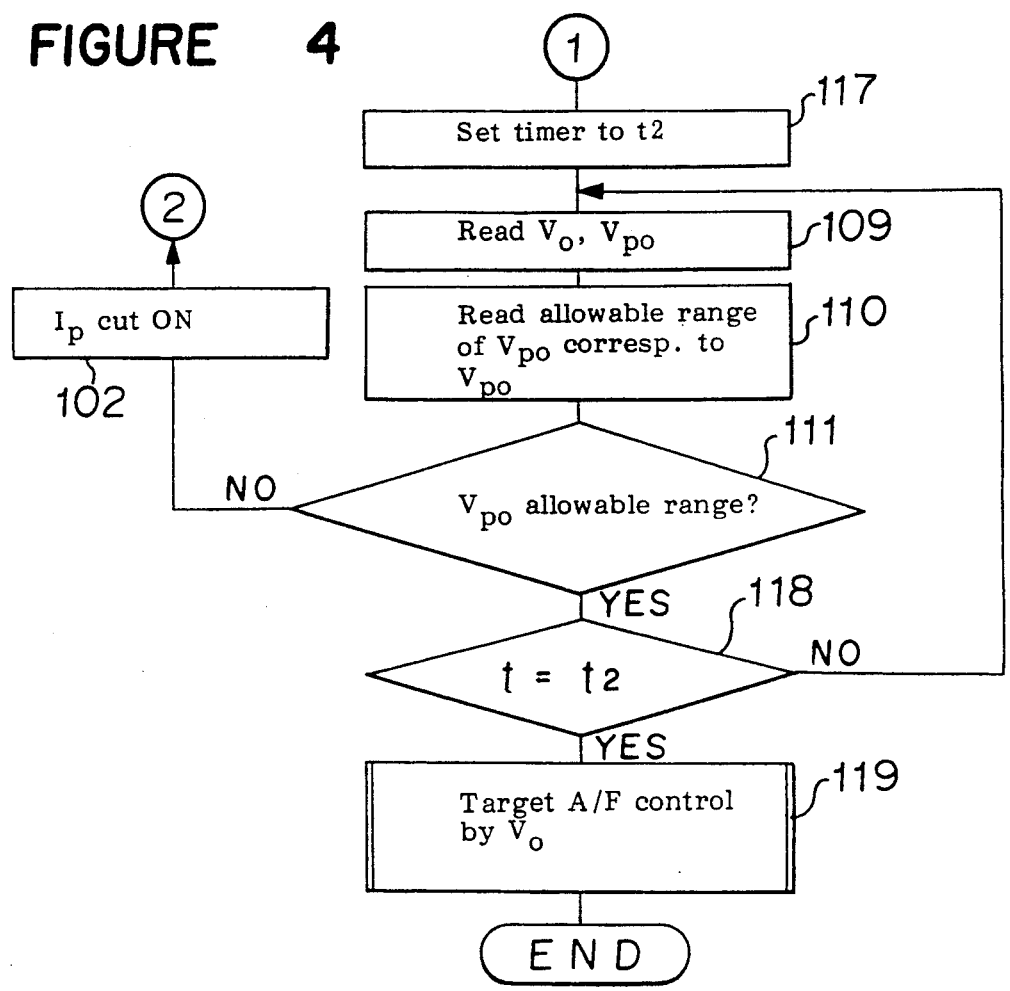
FIG. 4 is a flow chart showing a third example of a procedure for determining the activation of the device for measuring the activation of the air-fuel ratio sensor according to the present invention.

Next, explanation will be given a third example of this invention. FIG. 4 is a flow chart showing a procedure of determining the activation according to the third example. After the pump-current-cut state is released by the determination of the activation utilizing the time t1, in step 117, the operation sets the time t2. The operation similarly reads the air-fuel ratio output $V_O$ and the pump voltage output $V_{PO}$ in the period of the time t2, in step 109. In steps 110 and 111, the operation determines whether the pump voltage output $V_{PO}$ falls in the allowable pump voltage range.

When this pump voltage output $V_{PO}$ is out of the allowable pump voltage range, the operation performs the pump current cutting, and resets the time t1. Only when the pump voltage output $V_{PO}$ is in the allowable pump voltage range, and time t2 elapses in step 118, the operation performs the target air-fuel ratio control utilizing the air fuel ratio output $V_O$ in step 119.

Accordingly, in the case of this third example, after the determination of the activation at the sensor element temperature of about 500° C. utilizing the time t1, is performed, the operation awaits for the time t2 until time elapses and the sensor temperature reaches about 700° C. wherein the air-fuel ratio output $V_O$ is stabilized. Therefore, there is an advantage wherein inactivation of the sensor can clearly be detected, even when the sensor element temperature is lowered by the change of the running condition of the engine during that period.

Furthermore, in the example shown in FIG. 4, a case is shown wherein the period of the time t2 is made constant. However, as shown in FIG. 3, the period of the time t2 may be a decreasing function of the cooling water temperature TW, and the determination whether the pump voltage output $V_{PO}$ falls in the allowable pump voltage range, may be performed by utilizing the target air-fuel ratio AFO as in FIG. 3.

As stated above, according to the present invention, the power supply to the heater by the heater power supplying means in the pump-current-cut state, is initiated. The pump current cutting is released for a predetermined time from the starting time at every predetermined period, by the timer means. In this way, the pump current control is performed and the pump voltage is measured. When this pump voltage falls in a previously memorized pump voltage allowable range, the air-fuel ratio sensor is determined to be activated, and the pump-current-cut state is released. Therefore, the air-fuel ratio sensor is not deteriorated and destructed by the treatment of the activation determination and the activation determination can accurately be performed irrespective of the starting air-fuel ratio.

I claim:

1. A device for determining activation of an air-fuel ratio sensor which comprises:

an air-fuel ratio sensor comprising an oxygen concentration cell element and an oxygen pump element arranged at an exhaust system of an engine made of an oxygen-ion-conductive-solid-electrolyte material respectively provided with electrodes and interposing a diffusion chamber wherein exhaust gas of the engine is diffused and introduced, and a heater which heats the oxygen concentration cell element and the oxygen pump element;

a pump current controlling means for controlling pump current which flows in the oxygen pump element so that electromotive force of the oxygen concentration cell element becomes a predetermined reference voltage;

a pump current detecting means for detecting the pump current controlled by the pump current controlling means;

a pump current cutting means for cutting supply of the pump current;

a pump voltage detecting means for detecting pump voltage applied to the oxygen pump element;

a heater power supplying means for supplying power to the heater;

a memorizing means for previously memorizing a pump voltage allowable range for the pump current or a target air-fuel ratio of the engine;

a timer means for starting supplying power to the heater from the heater supplying power means in a pump-current-cut state and for releasing the cutting supply of the pump current during a predetermined time interval from starting time of supplying power at every predetermined time period; and an air-fuel ratio controlling device which has the pump current controlling means control the pump current, detects a pump voltage, determines that the air-fuel sensor is activated when the pump voltage falls in the previously memorized pump voltage allowable range, and releases the pump-current-cut state.

* * * * *